(12) United States Patent
Gustavsson

(10) Patent No.: US 11,013,887 B2
(45) Date of Patent: *May 25, 2021

(54) CATHETER ASSEMBLY WITH RESEALABLE OPENING

(71) Applicant: DENTSPLY IH AB, Mölndal (SE)

(72) Inventor: Evelina Gustavsson, Onsala (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/541,994

(22) Filed: Aug. 15, 2019

(65) Prior Publication Data

US 2019/0366034 A1    Dec. 5, 2019

Related U.S. Application Data

(63) Continuation of application No. 14/485,997, filed on Sep. 15, 2014, now Pat. No. 10,384,033, which is a
(Continued)

(30) Foreign Application Priority Data

Dec. 27, 2011 (EP) ..................... 11195736

(51) Int. Cl.
*A61M 25/00* (2006.01)
*B65D 75/00* (2006.01)
(Continued)

(52) U.S. Cl.
CPC ...... *A61M 25/002* (2013.01); *A61M 25/0017* (2013.01); *A61M 25/0045* (2013.01);
(Continued)

(58) Field of Classification Search
CPC ............ A61M 25/002; A61M 25/0017; A61M 2025/0046; A61M 25/0045; A61B 50/30; B65D 75/58; B65D 75/5833
(Continued)

(56) References Cited

U.S. PATENT DOCUMENTS 3,035,691 A    5/1962 Rasmussen et al.
3,761,013 A *  9/1973 Schuster ............. A61M 25/002
                                              206/439
(Continued)

FOREIGN PATENT DOCUMENTS

EP    217771     12/1991
EP    2072075    6/2009
(Continued)

OTHER PUBLICATIONS

Office Action for Brazilian Patent Application No. BR112014015867-3, dated Oct. 21, 2019, with translation (8 pages).
(Continued)

*Primary Examiner* — Steven A. Reynolds
(74) *Attorney, Agent, or Firm* — Perkins Coie LLP

(57) ABSTRACT

A medical device assembly is disclosed, including a medical device, preferably having a hydrophilic surface coating, and a package accommodating said medical device. The package if formed of two sheets of foil material, a first foil of which has been deep drawn into a trough shape, the package further including a resealable opening arranged within the bounds of the second foil. The medical device may e.g. be a urinary catheter.

22 Claims, 2 Drawing Sheets

Related U.S. Application Data continuation of application No. 13/714,940, filed on Dec. 14, 2012, now abandoned.

(60) Provisional application No. 61/580,464, filed on Dec. 27, 2011.

(51) Int. Cl.
  *B65D 75/58* (2006.01)
  *B65B 5/02* (2006.01)

(52) U.S. Cl.
  CPC .............. *B65B 5/02* (2013.01); *B65D 75/00* (2013.01); *B65D 75/58* (2013.01); *A61M 2025/0046* (2013.01)

(58) Field of Classification Search
  USPC ............ 206/364, 210, 571, 438, 205; 383/5; 604/544
  See application file for complete search history.

(56) References Cited

U.S. PATENT DOCUMENTS

| | | | |
|---|---|---|---|
| 3,967,728 A | 7/1976 | Gordon et al. | |
| 4,552,269 A | 11/1985 | Chang | |
| 4,568,334 A | 2/1986 | Lynn | |
| D300,947 S | 5/1989 | Utas-Sjoberg | |
| 4,894,059 A * | 1/1990 | Larsen | A61F 5/453 206/229 |
| 4,923,061 A | 5/1990 | Trombley, III | |
| D311,064 S | 10/1990 | Utas-Sjoberg | |
| D325,526 S | 4/1992 | Deguchi et al. | |
| 5,163,554 A | 11/1992 | Lampropoulos et al. | |
| 5,226,530 A | 7/1993 | Golden | |
| 5,309,604 A | 5/1994 | Poulsen | |
| 5,330,464 A | 7/1994 | Mathias et al. | |
| 5,344,011 A | 9/1994 | DiBernardo | |
| 5,366,444 A | 11/1994 | Martin | |
| 5,407,070 A | 4/1995 | Bascos | |
| D364,491 S | 11/1995 | Bradfield et al. | |
| 5,848,691 A | 12/1998 | Morris et al. | |
| 5,895,374 A | 4/1999 | Rodsten | |
| 6,409,717 B1 | 6/2002 | Israelsson et al. | |
| 6,594,971 B1 | 7/2003 | Addy et al. | |
| D490,302 S | 5/2004 | Nestenborg | |
| D491,803 S | 6/2004 | Nestenborg | |
| D496,266 S | 9/2004 | Nestenborg | |
| D498,671 S | 11/2004 | Nestenborg | |
| D498,672 S | 11/2004 | Nestenborg | |
| D499,016 S | 11/2004 | Nestenborg | |
| D499,017 S | 11/2004 | Nestenborg | |
| D499,335 S | 12/2004 | Nestenborg | |
| D499,643 S | 12/2004 | Nestenborg | |
| 6,849,070 B1 | 2/2005 | Hansen et al. | |
| D503,335 S | 3/2005 | Risberg et al. | |
| D505,067 S | 5/2005 | Nestenborg | |
| D534,649 S | 1/2007 | Haga et al. | |
| 7,476,223 B2 | 1/2009 | McBride | |
| D595,842 S | 7/2009 | Haga et al. | |
| D610,445 S | 2/2010 | Kedem | |
| 7,770,726 B2 | 8/2010 | Murray et al. | |
| D623,535 S | 9/2010 | Nilsson et al. | |
| 7,823,722 B2 | 11/2010 | Bezou et al. | |
| 7,857,770 B2 | 12/2010 | Raulerson et al. | |
| 8,052,673 B2 | 11/2011 | Nestenborg | |
| D699,559 S | 2/2014 | Gustavsson | |
| D734,165 S | 7/2015 | Kearns et al. | |
| D746,152 S | 12/2015 | Murray et al. | |
| D747,184 S | 1/2016 | Murray et al. | |
| D752,452 S | 3/2016 | Kearns et al. | |
| D764,943 S | 8/2016 | Murray et al. | |
| D775,522 S | 1/2017 | Gustavsson | |
| 10,384,033 B2 * | 8/2019 | Gustavsson | A61M 25/002 |
| 2001/0001443 A1 * | 5/2001 | Kayerod | A61M 25/002 206/364 |
| 2002/0130059 A1 | 9/2002 | Armijo | |
| 2003/0055403 A1 | 3/2003 | Nestenborg et al. | |
| 2003/0083644 A1 | 5/2003 | Avaltroni | |
| 2003/0168365 A1 | 9/2003 | Kaem | |
| 2005/0061698 A1 | 3/2005 | Delaney et al. | |
| 2005/0070882 A1 | 3/2005 | McBride | |
| 2005/0178684 A1 | 8/2005 | Kesler et al. | |
| 2006/0186010 A1 | 8/2006 | Warnack et al. | |
| 2006/0278546 A1 | 12/2006 | State et al. | |
| 2006/0278547 A1 | 12/2006 | Rowe et al. | |
| 2006/0289336 A1 | 12/2006 | Ford | |
| 2008/0051763 A1 | 2/2008 | Frojd | |
| 2008/0183181 A1 | 7/2008 | Treacy et al. | |
| 2008/0200907 A1 | 8/2008 | Nestenborg | |
| 2009/0163884 A1 | 6/2009 | Kull-Osterlin et al. | |
| 2009/0200186 A1 | 8/2009 | Nestenborg et al. | |
| 2011/0056825 A1 | 3/2011 | Baubet et al. | |
| 2011/0056852 A1 * | 3/2011 | Frojd | B65B 5/04 206/210 |
| 2011/0114520 A1 | 5/2011 | Matthison-Hansen | |
| 2011/0295239 A1 | 12/2011 | Gustavsson | |
| 2012/0037525 A1 | 2/2012 | Peck et al. | |
| 2012/0165790 A1 | 6/2012 | Gustavsson et al. | |
| 2012/0172846 A1 | 7/2012 | Nakamoto et al. | |
| 2012/0181193 A1 | 7/2012 | Wu | |
| 2012/0261290 A1 | 10/2012 | Limjaroen et al. | |
| 2013/0006226 A1 | 1/2013 | Hong et al. | |

FOREIGN PATENT DOCUMENTS

| | | |
|---|---|---|
| EP | 2106821 | 10/2009 |
| EP | 2292293 | 3/2011 |
| EP | 2389972 | 11/2011 |
| JP | 63-38470 | 2/1988 |
| JP | 3-501570 | 4/1991 |
| JP | 2001500414 | 1/2001 |
| JP | 2011139882 | 7/2011 |
| WO | 1989004685 | 6/1989 |
| WO | 1998011932 | 3/1998 |
| WO | 2010006620 | 1/2010 |
| WO | 2011058397 | 5/2011 |

OTHER PUBLICATIONS

European Search Report, Application No. 11195739.5, Publication May 24, 2012.

Office Action for Japanese Patent Application No. 2014-549436, dated Dec. 6, 2016 (10 pages).

Office Action for Chinese Patent Application No. 201280055819.7, dated Sep. 27, 2016 (12 pages).

Office Action for Japanese Patent Application No. 2014-549436, dated Oct. 10, 2017, with translation (10 pages).

European Search Report, Application No. 11195736.1, Search completed May 10, 2012.

Extended European Search Report dated Oct. 16, 2020 for European Patent Application No. 20179885.7 (9 pages).

* cited by examiner under U.S. patent application Ser. No. 14/485,997, filed Sep. 15, 2014, which is a continuation of U.S. patent application Ser. No. 13/714,940, filed Dec. 14, 2012, now abandoned, which further claims the benefit of and priority to European Application No. 11195736.1, filed on Dec. 27, 2011, and U.S. Provisional Patent Application No. 61/580,464, filed on Dec. 27, 2011, which are herein incorporated by reference for all purposes.

FIELD OF THE INVENTION

The present invention relates to a medical device assembly comprising a medical device and a resealable package accommodating the medical device. Specifically, the invention pertains to a medical device having a hydrophilic surface coating, wherein the assembly also includes a wetting fluid for activation of the hydrophilic surface coating. The invention is particularly related to catheters, and specifically to urinary catheters.

BACKGROUND OF THE INVENTION

The present invention relates to a medical device assembly, and in particular for urinary hydrophilic catheters. Catheters are commonly used for draining bodily fluids, e.g. from the bladder. Urinary catheters are e.g. used by a large group of persons for intermittent catheterization, which is a daily-life procedure, taking place several times a day. Typically catheters for intermittent catheterization are used by patients suffering from urinary incontinence or by disabled individuals like para- or tetraplegics. Using an intermittent catheter, the bladder may be drained through a natural or artificial urinary canal. Many catheters for intermittent catheterization are provided with a hydrophilic coating or the like, providing a smooth and slippery surface when wetted, for safe and comfortable insertion in the urinary canal.

Many hydrophilic catheter assemblies include a supply of wetting fluid, either in direct contact with the catheter or in a separate compartment, for clean and convenient activation of the hydrophilic surface before use.

However, there is still a need for improved packages for such catheter assemblies. The package should preferably be relatively simple and cost-efficient to produce. Further, the package should be easy to open, even for users with reduced dexterity. Still further, the package should enable adequate wetting of the catheter, and handling of the package in a clean manner. The package should also preferably be rather small, so that it can easily be carried around by the user in his/her daily life. It would also be highly advantageous if the package is resealable, so that the catheter package could be re-closed after use, if it cannot be immediately disposed of. In particular, it would be advantageous if the package would be resealable to enclose also a wet product and/or a wetting fluid without any risk for spillage.

Patent application US 2011/056852 by the same applicant discloses a urinary catheter assembly having a resealable opening. However, even though this catheter assembly is highly useable for short catheters, for female users, re-insertion of longer catheters, typically for male users, may be cumbersome and with the risk of spillage and the like.

CATHETER ASSEMBLY WITH RESEALABLE OPENING

CROSS-REFERENCE TO RELATED APPLICATIONS

This patent application is a continuation of U.S. patent application Ser. No. 14/485,997, filed Sep. 15, 2014, which is a continuation of U.S. patent application Ser. No. 13/714,940, filed Dec. 14, 2012, now abandoned, which further Male catheters may be 40 cm long, or even longer, and insertion of the tip portion through the resealable opening without touching the insertable part of the catheter is rather difficult, especially for users with reduced dexterity. Further, closing of the resealable opening after re-insertion of the catheter in a sufficiently sealed manner may also be difficult with this known catheter assembly, and again, especially for users with reduced dexterity. There is therefore a need for a catheter assembly with resealable opening enabling easier re-insertion of the catheter.

Many other types of medical devices face similar problems.

In conclusion there is still a need for an improved medical device assembly of the above discussed general type.

SUMMARY OF THE INVENTION

It is therefore an object of the present invention to provide a medical device assembly which at least alleviates the above-discussed problems.

This object is obtained by means of a medical device assembly and a method in accordance with the appended claims.

According to a first aspect of the invention, there is provided a medical device assembly comprising a medical device, and preferably a urinary catheter, and also preferably having a hydrophilic surface coating, and a package accommodating said medical device, wherein the package is formed of two sheets of foil material, a first foil of which has been deep drawn into a trough shape, the package further comprising a resealable opening arranged within the bounds of the second foil.

In the context of the present application, "resealing" relates to closure of a previously opened opening, wherein the closure forms closure that at least to a large extent prevents liquid from leaking out from the closure.

In the context of the present application, "deep drawn" defines any process forming a permanent deformation of a plastic material, such as vacuum forming and other types of thermoforming by means of heating, and the like. In a preferred embodiment, vacuum forming is used. In vacuum forming, the sheet is heated to a forming temperature, stretched onto or into a single-surface mold, and held against the mold by applying vacuum between the mold surface and the sheet. The mold may e.g. be a cast or machined aluminum mold, or a composite mold.

In the context of the present application, "trough" defines a shape having a rim, thin or wide, encircling a lowered middle section.

The rim is preferably provided with an essentially planar edge portion, encircling the lowered middle section. The depth of the lowered middle section is preferably sufficient to entirely accommodate the height of the medical device and/or the height of a wetting fluid container. Preferably, the depth is in the range 0.2-3 cm, and preferably in the range 0.5-2 cm, and most preferably in the range 0.7-1.5 cm. It is further possible to have different depths in different parts of the package. For example, a part housing anon-insertable catheter end, and optionally a wetting fluid container, may have a greater depth than a part housing an insertable part of a catheter.

The second foil is preferably not deep-drawn. Instead, this foil is preferably essentially planar, or only slightly curved.

This package is very well suited for use for catheters, and in particular hydrophilic catheters, i.e. catheters being provided with a hydrophilic surface coating or catheters being made of a hydrophilic material. The package enables easy, clean and efficient wetting and handling of the hydrophilic catheter, and also provides sterile conditions for the entire wetting process. At the same time the package is relatively simple and cost-efficient to produce. In particular, the catheter assembly is well-suited for the type of assemblies including a hydrophilic catheter and a wetting fluid being accommodated by the package. The wetting fluid may e.g. be arranged directly in contact with the hydrophilic surface of the catheter, or in a separate compartment of the package or in a separate container being housed by the package.

Since the resealable opening is arranged in a non-deep drawn, and preferably essentially planar sheet, opening and re-closing of the resealable opening is greatly facilitated. It has been found by the present inventor that re-arranging a resealable opening into a sealed and sufficiently closed condition is much simpler on a planar or only slightly curved surface than on surfaces curved in one or several directions. This is particularly advantageous for users having reduced dexterity.

Further, during manufacturing, formation of the resealable opening is also facilitated, enabling a more cost-efficient production.

Still further, since the first sheet underlying the second sheet with the resealable opening is deep drawn into a trough shape, a spacing between the first and second sheets are formed and continuously maintained. This spacing essentially corresponds to the depth of the lowered middle section of the deep drawn trough. Hereby, it is avoided that the catheter deforms the second sheet to any significant degree. It is further ensured that there is a spacing between the sheets also after withdrawal of the catheter from the package. This greatly facilitates re-insertion of the medical device, since re-insertion of the medical device hereby does not necessitate separation of the sheets. Instead, the medical device may simply be guided through the resealable opening into the already available compartment formed between the sheets. This is particularly advantageous for use with relatively long medical devices, such as long catheters, when manipulation of the tip portion of the catheter by holding the rearward connector end is complicated if it involves any other actions than simply guiding the tip into a preformed compartment of sufficient dimensions. Further, this simplified re-insertion is highly advantageous for users with reduced dexterity.

Preferably, the medical device is a hydrophilic urinary catheter for intermittent use. However, even though the catheter assembly is at present primarily intended for urinary hydrophilic catheters, where the package also includes a wetting fluid, the catheter assembly may also be used for other types of catheters. For example, the catheter may be other types of catheters, such as vein catheters and the like. Further, the catheter may be provided with other types of lubricious coatings, such as gel lubricants and the like, or being without any surface coating at all. Still further, assemblies without a wetting fluid are also feasible. Still further, the assembly of the present invention may also be used for other types of medical devices than catheters.

The two sheets of foil material are preferably joined along the edges of the foils, and preferably connected around the edges by means of welding. Preferably, the first and second sheet materials comprise laminated sheets, having a weldable inner layer and a protective outer layer.

The resealable opening is preferably arranged at, and preferably overlying, the part of the package housing the non-insertable, rearward end of the medical device/catheter. Hereby, the medical device/catheter may be withdrawn with the connector end first, which enables a clean and convenient way of handling the catheter without touching the insertable part directly by hand.

Preferably, the resealable opening is arranged as a peel opening. Most preferably, the resealable opening in the second sheet may comprise a perforation line extending along a non-closed loop in one of said sheets, said perforation line defining a flap opening, and a third sheet connected by means of an adhesive over said flap opening, wherein said third sheet with a margin covers the entire flap opening. The third sheet further preferably forms a tab not provided with adhesive, said tab providing a grip portion for peel opening of the package.

By "perforation" is meant a diminished material thickness, possibly extending over the entire thickness, providing a complete cut-through. By means of "perforation line" is meant a line with continuous or discontinous perforations. Thus, in the context of the present application, "perforation line" is used to indicate a line forming a weakening, such as a total cut-through, a partial cut-through, point perlorations, or the like, forming a weakening where a rupture will occur when a force is exerted on the material.

Such a resealable opening is efficient and easy to use, and also relatively simple to produce. The tab enables a vecy simple peel-opening of the package. At the same time, the flap opening provides an efficient way of removing the medical device, and also for resealing of the package, once the medical device has been used and been replaced in the package.

In production, one of the first and second sheets may be provided with the non-closed loop perforation line, by means of cutting or the like, and the third sheet material can thereafter be adhered on top of it. Alternatively, the third sheet material can be added first and the perforated line (or total cut) could be formed afterwards.

The adhesive is preferably adapted to maintain a sterile closure of the package before use, and to be resealable after use.

The non-closed loop defining the flap opening preferably debouches towards (i.e. faces) the end of the package housing the insertion end of the medical device/catheter. Hereby, the tab is arranged close to the end of the package, and the peeling occurs downwards, towards the insertion end of the medical device/catheter, which is efficient for avoiding spillage of the wetting fluid within the package after activation, especially when the medical device assembly is hanged, adhered or otherwise arranged in a vertical direction during withdrawal from the package and re-insertion into the package.

The third sheet preferably covers the entire flap opening with a margin exceeding 2 mm, and preferably exceeding 5 mm. Hereby, a sterile seal may be obtained before opening of the package, and at the same time an adequate resealing capability may be obtained.

The non-closed loop of the perforation line preferably forms a tongue directed inwardly towards the non-closed opening of the non-closed loop.

Further, the non-closed loop preferably has loop ends directed towards the interior of the non-closed loop. Hereby, it is efficiently avoided that the third material sheet is peeled off completely.

The third sheet further preferably comprises a weakened area forming a seal integrity mark. Hereby, it is ensured that the seal has not been broken before use, ensuring full integrity of the product. Preferably, the seal integrity mark is arranged between the tab and the part of the third sheet overlying the perforation line.

Preferably a wetting fluid is also included in the assembly. The wetting fluid may be arranged in direct contact with the hydrophilic surface of the medical device. However, preferably the wetting fluid is arranged separately from said medical device within the package. The separate arrangement of the wetting fluid can be obtained by means of closed compartment within the package. However, in a preferred embodiment, the wetting fluid is arranged in a wetting fluid container arranged within said package, such as in a pouch, sachet or the like. In case the wetting fluid is arranged separately, the container or compartment is openable into the part of the package housing the medical device, in order to enable release of the wetting fluid into contact with the hydrophilic part of the medical device before use. Release of the wetting fluid can be obtained by squeezing, bending or the like, as is per se well known in the art.

The medical device assembly may further comprise a fourth sheet arranged on the first sheet, on the side of said package being opposed to the resealable opening, said fourth sheet being connected by means of an adhesive to said first sheet, and forming a tab not provided with adhesive, said tab providing a grip portion for exposure of said adhesive to form a holding arrangement for said package. By means of this fourth sheet material, the medical device assembly may e.g. be attached to a sink, a wall or the like, which enables very efficient and easy handling of the product, even for user with reduced dexterity.

The package is preferably elongate, and preferably narrowly surrounding the medical device and the optional wetting fluid compartment. For example, the package may have an essentially rectangular form in the forward section, and a larger and also essentially rectangular form in the rearward section. Hereby, a very cost-efficient and compact product is obtained.

According to a second aspect of the invention, there is provided a method of producing a medical device assembly comprising the steps:

providing a medical device, preferably a hydrophilic catheter, i.e. a catheter having a hydrophilic surface coating or being made by a hydrophilic material; and accommodating the medical device, and optionally also a wetting fluid, in a package, said package comprising:

a first and a second sheets of foil material connected around the edges, a first of which has been deep drawn into a trough shape, the package further comprising a resealable opening arranged within the bounds of the second foil.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DESCRIPTION OF PREFERRED EMBODIMENTS

Figure 1:
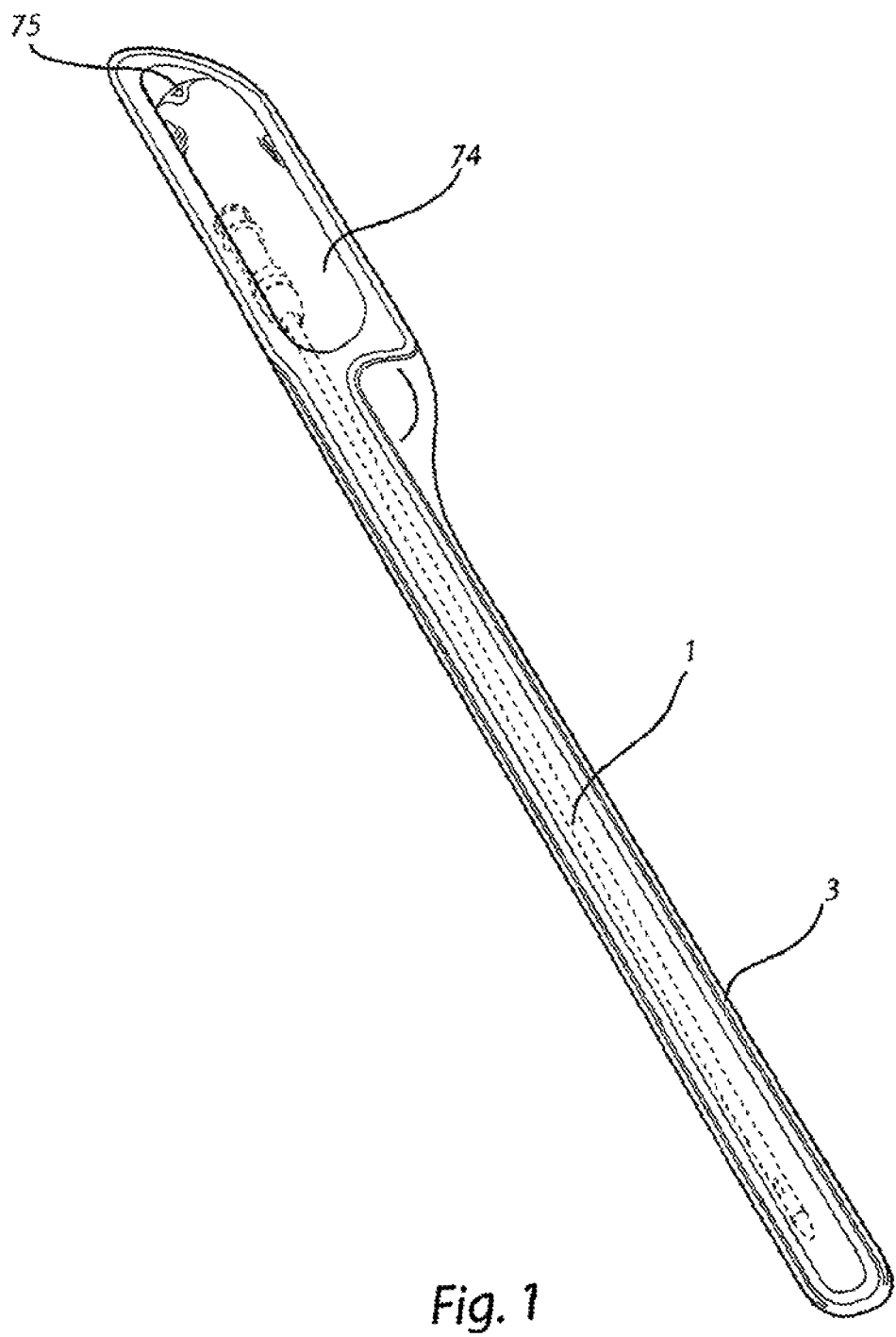
FIG. 1 illustrates a perspective view of a medical device assembly in accordance with an embodiment of the present invention.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the medical device, etc.

The medical device assembly can be used for many types of medical devices. However, it is particularly suited for catheters. Catheters may be used for many different purposes, and for insertion into various types of body-cavities. However, the following discussion is in particular concerned with the preferred field of use, hydrophilic urinary catheters, even though the invention is not limited to this particular type of catheters, and also not to catheters.

Figure 2:
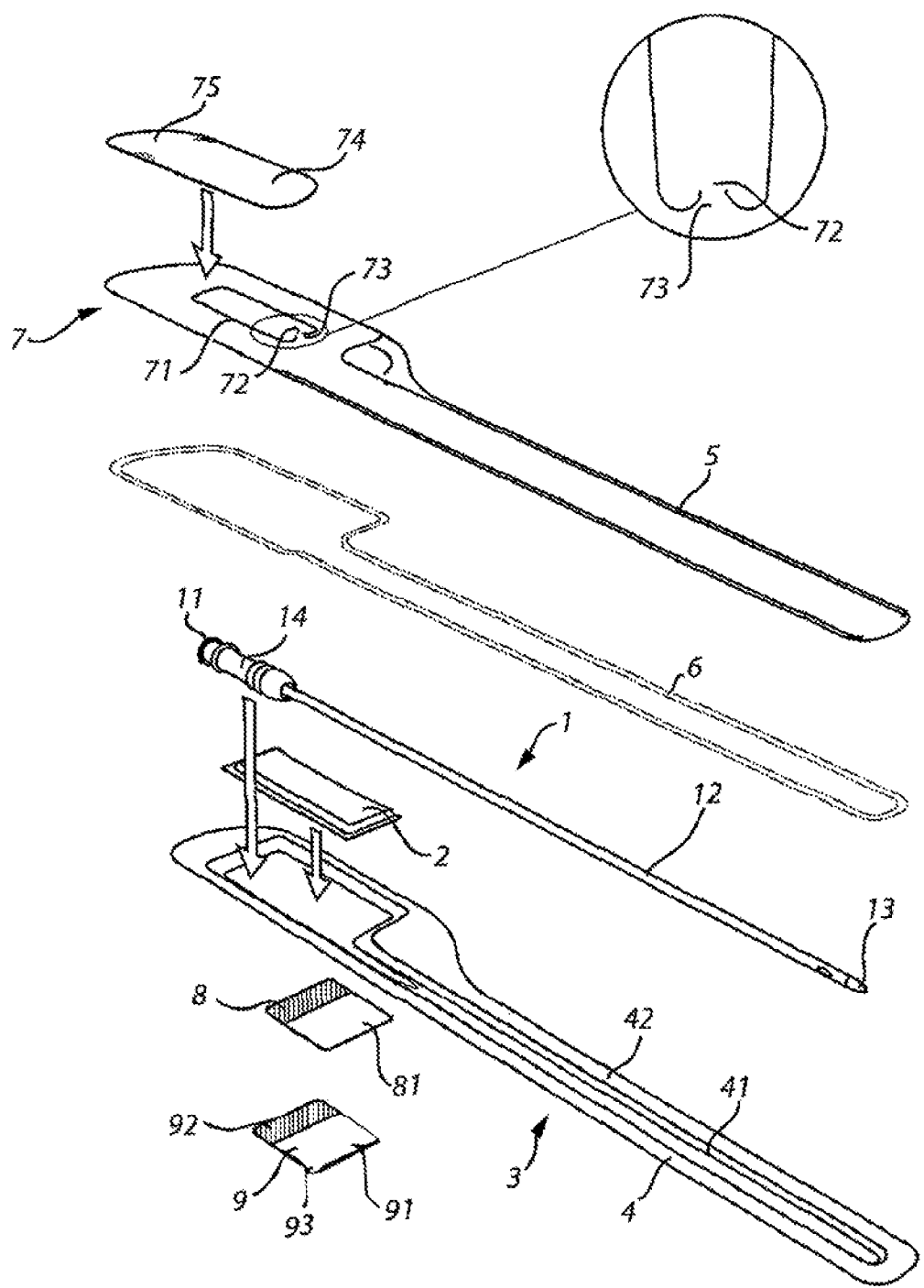
FIG. 2 illustrates an exploded view of the medical device assembly in FIG. 1.

The catheter assembly as illustrated in FIGS. 1-2 comprises a catheter 1 having a hydrophilic surface coating, a wetting fluid for activation of said hydrophilic surface coating and a package 3 accommodating the catheter and the wetting fluid.

The catheter 1 may be any type of hydrophilic catheter, as is per se well known in the art. Preferably, the catheter comprises a flared rearward portion, forming a flared connector 11, and an elongated shaft 12, connected to the flared connector 11, and in the opposite end having a catheter insertion end 13.

An applicator 14, in the form of e.g. a tube, sleeve or cuff, may be releasably attached to the connector 11, in order to be release from the connector prior to insertion, and to aid in manipulating the catheter during insertion without directly contacting the catheter surface.

At least a part of the elongate shaft 12 forms an insertable length to be inserted through a body opening of the user, such as the urethra in case of a urinary catheter. By insertable length is normally, in the context of a hydrophilic catheter, meant that length of the elongate shaft 12 which is coated with a hydrophilic material, for example PVP, and which is insertable into the urethra of the patient. Typically, this will be 50-140 mm for a female patient and 200-350 mm for a male patient. Even though PVP is the preferred hydrophilic material, other hydrophilic materials may be used, such as hydrophilic polymers selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The coating may also comprise an osmolality-increasing compound, as is e.g. taught in EP 0 217 771.

The wetting fluid is preferably arranged separate from the catheter, in a wetting fluid container 2, such as a pouch or a sachet. The wetting fluid container is openable by means of e.g. exerting a pressure to the container, whereby the wetting fluid is released into the package, thereby wetting the hydrophilic surface of the catheter. The wetting fluid is preferably a liquid, and most preferably an aqueous liquid, such as water or saline. Such wetting fluid containers and wetting fluids are per se well known in the art. The flexible material used for wetting fluid pouch is preferably a flexible material which provides a moisture barrier or low water vapor transmission. The flexible material may e.g. comprise or consist of one or several of aluminum, aluminum oxide, silicone oxide, metallocene polyvinylidene chloride (PVdC) and poly(ethylene-vinylalcohol) (EVOH). For example, the flexible material can be made as coextruded polyolefines with polyamides, poly(ethylene-terephthalate) (PET), including barrier resins such as polyvinylidene chloride (PVdC) or poly(ethylene-vinylalochol) (EVOH). However, other materials exhibiting similar properties are also feasible.

The wetting fluid may be any fluid that wets a hydrophilic surface of the catheter.

Preferably, the wetting fluid container 2 is arranged close to, and most preferably overlying, the connector end of the catheter.

The package comprises a first sheet material 4 and a second sheet material 5, connected around the edges to form an inner cavity housing the catheter and the wetting fluid. The first and second sheet materials are preferably connected around the edges by means of welding, forming a welded edge joint 6. Preferably, the first and second sheet materials comprise laminated sheets, having a weldable inner layer and a protective outer layer.

The sheet materials are preferably of a flexible plastics material. The material may be transparent, but opaque or semi-opaque materials may also be used. For example, the sheets can be made of polymer materials such as polyethene (PE), polypropylene {PP), polyamide (PA), poly(ethylene terephthalate) (PET), oriented polypropylene (OPP), oriented polyamide (OPA), etc. Also, the receptacle can be made from a lammate of such polymer materials and/or aluminum, aluminum oxide or other materials functioning as barrier materials.

The first sheet material 4 is deep drawn into a trough shape, thereby forming an upper rim 41, to be m contact with the second sheet material 5, and a lower middle section, formed to accommodate the catheter and the wetting fluid sachet. The rim is preferably provided with an essentially planar edge 42 surrounding the lowered middle section. The planar edge may have any dimensions, such as being very thin or being relatively wide. Further, the planar edge may have various dimensions around the circumference. The second sheet material 5 is preferably essentially planar, or only slightly curved.

The second sheet material 5 comprises a resealable opening 7. The resealable opening preferably comprises a perforation line 71 in the second sheet material, extending along a non-closed loop defining a flap opening. The non-closed loop defining the flap opening is preferably arranged over the connector end of the catheter 1. Further, the non-closed loop preferably has an opening 72 debouching towards the end of the package housing the insertion end of the catheter. At the end, the non-closed loop preferably forms a tongue 73 directed inwardly towards the non-closed opening of the non-closed loop. The loop ends, at the opening 72, are preferably directed towards the interior of the non-closed loop.

The non-closed loop generally forms a C- or U-shape.

The resealable opening further preferably comprises a third sheet material 74, arranged over the non-closed loop, and connected to the second sheet material 5 by means of an adhesive. The third sheet material is preferably arranged to cover the entire flap opening with a margin, preferably exceeding 2 mm, and most preferably exceeding 5 mm. An end of the third sheet material is not adhered to the first sheet material, and forms a tab 75 providing a grip portion for peel opening of the package. The tab is preferably arranged in the end directed towards the insertable part of the catheter. Further, the tab may be provided with gripping means to facilitate gripping of the tab. The gripping means may e.g. be one or several of a surface coating, surface roughening, corrugations, embossment, perforations or a larger gripping opening, etc.

The adhesive is adapted to maintain a sterile closure of the package before use, and to be resealable after use. The adhesive preferably has a strength to withstand a pulling force in the range of 3-10 N. The adhesive can e.g. be an acrylate emulsion, or an acrylate based hot melt adhesive.

The third sheet material further preferably comprises a weakened area forming a seal integrity mark. Hereby, it is ensured that the seal has not been broken before use, ensuring full integrity of the product. Preferably, the seal integrity mark is arranged between the tab and the part of the third sheet material overlying the perforation line. The weakened area preferably comprises weakened or perforated lines arranged in a pattern, e.g. as illustrated in the drawings, making part of the third sheet material to remain adhered to the first sheet material during peel off of the third sheet material.

The catheter assembly may further comprise a fourth sheet material 8 arranged on the first sheet material, i.e. on the side of the package being opposed to the third sheet material and the resealable opening. The fourth sheet material is also connected by means of an adhesive to the package, and forms a tab 81 not provided with adhesive, said tab providing a grip portion for exposure of said adhesive to form a holding arrangement for the package. By means of this fourth sheet material, the catheter assembly may e.g. be attached to a sink, a wall or the like, which enables very efficient and easy handling of the product, even for user with reduced dexterity.

In order to ensure that the fourth sheet materials are not removed completely during peeling, perforated lines (not shown) may be arranged on one or preferably both of the sides. The perforated lines preferably extend from the outer side of the fourth sheet material, about in the center of the sheet material, towards the interior of the sheet in a direction away from the pulling tab. The tear line preferably ends in a hook or the like towards the side of the sheet, but not extending entirely to the side of the sheet.

Alternatively, the fourth sheet may comprise two separate sheets: An inner sheet 8, which is connected to the first sheet by means of e.g. adhesive 81, and an outer sheet 9, which is connected to the inner sheet. The connection between the inner and outer sheet may also be provided by means of adhesive 91. The adhesive may be provided on either the outer surface of the inner sheet or the inner surface of the outer sheet, or preferably on both. A tab 93 is provided in the outer sheet to allow for simple separation of the inner and outer sheets. In an area 92 opposite the tab 93, the connection between the inner and outer sheets is made stronger, e.g. by using a stronger adhesive. Hereby, separation of the two sheets, which is initiated by pulling the tab 93, is stopped at this area 92, and the exposed areas with adhesive on the inner and/or outer sheets may be used to attach the package to any suitable surface or object.

The third and fourth sheet materials may e.g. be of polypropene (polypropylene), polyester or polyethene (polyethylene).

In a preferred embodiment, the package is elongate, and preferably has an essentially rectangular forward part, in the form of an elongate pocket, and an enlarged rearward part. The enlarged rearward part may be rectangular or of other shapes, such as having rounded corners, etc. The enlarged rearward part is preferably dimensioned to accommodate the catheter connector and the wetting fluid container. The elongate pocket is preferably dimensioned to accommodate, and narrowly surround, the insertable part of the catheter. Hereby, a very compact product is obtained.

In use, the wetting fluid container is opened, for activation of the hydrophilic surface of the catheter. After sufficient wetting, the tab of the fourth sheet may be peeled, so that the catheter assembly can be connected to a sink or the like. The tab of the third sheet is peeled open, and the catheter is removed and used. Thereafter, the catheter may be re-inserted, and the package can then be closed, and stored for later disposal.

A method of manufacturing the above-discussed catheter assembly preferably comprises the following steps of producing the package, performed in any order:

Providing a first and second sheet material;
Deep drawing the first sheet into the appropriate trough shape.
Providing a resealable opening, e.g. by the sub-steps of:
    Providing the non-closed loop perforated line in the second sheet material by cutting the material;
    Providing third sheet materials;
    Optionally, providing the perforated lines in the third sheet material;
    Adhering the third sheet material to the first sheet material;
Connecting the first and second sheet material to each other along the edges, e.g. by means of welding;
Optionally, providing a hanging means, e.g. in the form of an adhesive, which may include the sub-steps:
    Providing one or two sheet(s) of a fourth sheet material;
    Optionally, providing the perforated lines in the fourth sheet material; and
    Adhering the fourth sheet material to the first sheet material.

In addition, the catheters and the wetting fluid container is provided and arranged within the package before the package is finally closed, and sterilization of the product is provided by means of e.g. radiation.

The third and fourth sheet material may be provided on large sheets, arranged on a layer of adhesive, and with the perforation lines pre-arranged before assembly.

Specific embodiments of the invention have now been described. However, several alternatives are possible, as would be apparent for someone skilled in the art. For example, although the wetting fluid in the described embodiments has been arranged separated from the catheter, in a wetting fluid container, it is also possible to arrange the wetting fluid in direct contact with the catheter, thereby always maintaining a ready-to-use state. Further, if a wetting fluid container is used, it is possible to arrange this container close to the connector end of the catheter, close to the insertion end of the catheter, or at any other location within the receptacle. Still further, resealable openings may be provided in other forms than in the above-indicated preferred embodiment. Further, a package without the fourth sheet is feasible, and other sheets may also be used. Further, other shapes for the various perforation lines are feasible. Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A medical device assembly, comprising:
    a urinary catheter including an insertion end and a non-insertion end, the catheter having a hydrophilic surface coating;
    a wetting fluid for activation of said hydrophilic surface coating; and
    a package accommodating the catheter and the wetting fluid, wherein the package comprises:
    a first sheet of material, having been deep drawn into a trough shape, and a second sheet of material, the package further comprising an opening arranged within the bounds of the second sheet of material, wherein:
    the second sheet of material is joined around an edge with an edge of the first sheet of material,
    the opening is arranged in a section of the package housing the non-insertion end of the catheter, and
    a third sheet of material is arranged over, and with a margin covering, said opening and connected to the second sheet of material with adhesive, thereby providing a resealable opening in the package; wherein the opening in the second sheet of material is formed as a perforation line extending along a non-closed loop, the perforation line defining a flap opening, wherein the non-closed loop defining the flap opening debouches towards the end of the package housing the insertion end of the catheter.

2. The medical device assembly of claim 1, wherein the first and the second sheets of material are connected together by welded joints.

3. The medical device assembly of claim 1, wherein the trough of the first sheet of material forms a narrow forward part of the package having first spaced wall portions for housing and narrowly surrounding the insertion end of the catheter and a wider rearward part of the package having second spaced wall portions for housing the non-insertable end of the catheter.

4. The medical device assembly of claim 1, wherein the second sheet of material is essentially planar.

5. The medical device assembly of claim 1, wherein the non-closed loop includes loop ends directed towards interior of the non-closed loop.

6. The medical device assembly of claim 1, wherein the adhesive is adapted to maintain a sterile closure of the package before use, and to be resealable after use.

7. The medical device assembly of claim 1, wherein the third sheet forms a first tab not provided with adhesive, said first tab providing a grip portion for peel opening.

8. The medical device assembly of claim 1, wherein the third sheet covers the opening with a margin exceeding 2 mm.

9. The medical device assembly of claim 1, wherein the wetting fluid is arranged separately from said catheter in the package.

10. The medical device assembly of claim 8, wherein the wetting fluid is arranged in a wetting fluid container within the package.

11. The medical device assembly of claim 1, wherein the wetting fluid is arranged in direct contact with the hydrophilic surface of the medical device to always maintain a ready-to-use state.

12. The medical device assembly of claim 1, further comprising a fourth sheet of material arranged on the first sheet, the fourth sheet located on a side of the package being opposed to the resealable opening.

13. The medical device assembly of claim 12, wherein the fourth sheet is connected to the first sheet by an adhesive, the fourth sheet including a second tab not provided with adhesive, the second tab providing a grip portion for exposure of the adhesive to form a holding arrangement for the package.

14. The medical device assembly of claim 1, wherein the first and second sheets comprise laminated sheets, having a weldable inner layer and a protective outer layer.

15. The medical device assembly of claim 1, wherein the first sheet further comprises a planar rim around a perimeter thereof.

16. The medical device assembly of claim 15, wherein the planar rim further comprises rounded corners.

17. The medical device assembly of claim 7, wherein the first tab is arranged in an end of the third sheet and is directed away from the end of the package housing the insertion end of the catheter.

18. The medical device assembly of claim 1, wherein the trough further comprises at least two depths, a first portion of the trough having a first depth and a second portion of the trough having a second depth.

19. The medical device assembly of claim 18, wherein the second depth is greater than the first depth, and wherein the insertion end of the catheter is housed in the first portion of the trough and the non-insertable end of the catheter is housed in the second portion of the trough.

20. The medical device assembly of claim 1, further comprising an applicator releasably attached to the non-insertable end of the catheter, arranged to be released prior to use to aid in manipulating the catheter during insertion without directly contacting the surface of the catheter.

21. The medical device assembly of claim 20, wherein the applicator is in the form of a tube, sleeve or cuff.

22. A medical device assembly, comprising:
   a urinary catheter including an insertion end and a non-insertion end, the catheter having a hydrophilic surface coating;
   a wetting fluid for activation of said hydrophilic surface coating; and
   a package accommodating the catheter and the wetting fluid, wherein the package comprises:
   a first sheet of material, which has been deep drawn into a trough shape, and a second sheet of material, the package further comprising an opening arranged within the bounds of the second sheet of material, wherein the second sheet of material is joined around an edge with an edge of the first sheet of material, wherein the opening is arranged in a section of the package housing the non-insertion end of the catheter, and wherein a third sheet of material is arranged over, and with a margin covering, said opening and connected to the second sheet of material with adhesive, thereby providing a resealable opening in the package, wherein the third sheet forms a first tab not provided with adhesive, said first tab providing a grip portion for peel opening, and wherein the first tab being arranged in an end of the third sheet is directed away from the end of the package housing the insertion end of the catheter when the resealable opening is closed and covered by the third sheet.

* * * * *